US012053318B2

(12) United States Patent
Sun et al.

(10) Patent No.: US 12,053,318 B2
(45) Date of Patent: Aug. 6, 2024

(54) LONG LENGTH IMAGING METHOD AND DEVICE BASED ON DIGITAL RADIOGRAPHY

(71) Applicant: CARESTREAM HEALTH, INC., Rochester, NY (US)

(72) Inventors: Ken Sun, Shanghai (CN); Mona Zhang, Shanghai (CN); Mingzhi Chen, Shanghai (CN); Xinyu Zhang, Bejing (CN); Minggang She, Shanghai (CN); Jun Liu, Hunan (CN)

(73) Assignee: Carestream Health, Inc., Rochester, NY (US)

( * ) Notice: Subject to any disclaimer, the term of this patent is extended or adjusted under 35 U.S.C. 154(b) by 298 days.

(21) Appl. No.: 17/672,835

(22) Filed: Feb. 16, 2022

(65) Prior Publication Data
US 2022/0280129 A1   Sep. 8, 2022

(30) Foreign Application Priority Data

Mar. 4, 2021   (CN) .......................... 202110240072.3

(51) Int. Cl.
| | |
|---|---|
| *A61B 6/00* | (2024.01) |
| *G06T 7/00* | (2017.01) |
| *G06T 7/12* | (2017.01) |
| *G06T 7/80* | (2017.01) |
| *G06V 40/10* | (2022.01) |
| *H04N 23/611* | (2023.01) |

(52) U.S. Cl.
CPC .............. *A61B 6/5241* (2013.01); *A61B 6/54* (2013.01); *G06T 7/0012* (2013.01); *G06T 7/12* (2017.01); *G06T 7/80* (2017.01); *G06V 40/103* (2022.01); *H04N 23/611* (2023.01); *G06T 2207/10116* (2013.01)

(58) Field of Classification Search
CPC ....... A61B 6/5241; A61B 6/54; A61B 6/4233; A61B 6/4452; A61B 6/52; A61B 6/40; A61B 6/42; A61B 6/469; A61B 6/5217; A61B 6/542; G06T 7/0012; G06T 7/12; G06T 7/80; G06T 2207/10116; G06T 7/30; G06V 40/103; G06V 10/16; H04N 23/611; H04N 23/60
See application file for complete search history.

(56) References Cited

U.S. PATENT DOCUMENTS

2017/0340299 A1*  11/2017  Grass ................... A61B 6/5205

\* cited by examiner

*Primary Examiner* — Kiho Kim

(57) ABSTRACT

A long-length imaging method based on digital radiography, a digital radiography device, an image processing system and a computer-readable memory medium to implement the method. The long-length imaging method comprises the following steps: A. determining a part of interest of an anatomy of an object; B. determining imaging parameters of digital radiography based on the part of interest, the imaging parameters at least including a plurality of specified positions of imaging components, wherein the plurality of specified positions are configured to capture X-ray images including the part of interest of the anatomy of the object; and C. generating a long-length image in relation to the part of interest of the anatomy of the object based on the captured X-ray images.

13 Claims, 10 Drawing Sheets

LONG LENGTH IMAGING METHOD AND DEVICE BASED ON DIGITAL RADIOGRAPHY

CROSS REFERENCE TO RELATED APPLICATIONS

This application claims priority to counterpart Chinese Patent Application No. 202110240072.3, filed Mar. 4, 2021, in the China National Intellectual Property Administration, in the name of Sun et al., and entitled METHOD AND SYSTEM FOR AUTOMATIC LONG LENGTH IMAGING.

TECHNICAL FIELD

This invention relates to digital radiography, especially to a long-length imaging method based on digital radiography as well as a digital radiography device, an image processing system and a computer-readable memory medium to implement the method.

BACKGROUND ART

As a clinic imaging tool, the DR (digital radiography) system is being employed widely in the medical domain and also in the industrial domain. As illustrated in FIG. 1, the radiation of an X-ray source 110 of a DR device 10 passes through a patient or object PA and beams onto a radiation detector 120, wherein the detector, for example, may include a scintillator screen 121 and an image sensing array 122. The scintillator screen 121 is intended to convert energy from ionization radiation to light radiation of different frequencies. And, the image sensing array 122 is usually mounted on the back of the scintillator screen or coupled optically to the scintillator screen, which, as such, receives emitted light excited by incident radiation and creates digital images. The digital images created this way may be processed and displayed by an image processing unit, and such functions are rendered normally by a computer work station and a display 130.

In many clinic applications, it is necessary to image a relatively large portion of body anatomy (e.g., the spine or a whole leg bone). Under the restraint of cost and technology, the size of a detector is greatly limited as well, which results in the complication in the process of long-length imaging. According to some long-length imaging technologies set forward to work with a DR system, a larger composite image is re-created by acquiring a series of exposures/images in different positions (a patient is required to remain still in such a process) and then stitching the individual images together. However, in the existing long-length imaging technologies, operators are required to set, according to experience, parameters such as exposure times or times of image capture and overlapping extent of images of two adjacent captures, so as to subsequently determine, based on the parameters, the initial position and the subsequent position of an X-ray source and a radiation detector. The introduction of human factors makes the operation complicated and cumbersome with an unstable imaging quality.

Thus, it is necessary to provide a long-length imaging method and device based on digital radiography to address the problem noted above.

SUMMARY IN INVENTION

This invention is intended to provide a long-length imaging method based on digital radiography, as well as a digital radiography device, an image processing system and a computer-readable memory medium to implement the method.

In the light of one aspect of the invention, the long-length imaging method based on digital radiography comprises the following steps:
   A. determining a part of interest of an anatomy of an object;
   B. determining imaging parameters of digital radiography based on the part of interest, the imaging parameters at least including a plurality of specified positions of imaging components, wherein the plurality of specified positions are configured to make X-ray images captured at the plurality of specified positions by using the imaging components include the part of interest of the anatomy of the object; and
   C. generating a long-length image in relation to the part of interest of the anatomy of the object based on the X-ray images at the plurality of specified positions.

Alternatively, step A of the long-length imaging method noted above comprises:
   A1. generating, from an image presenting external features of the object, a body pose image suitable to depict the anatomy of the object, the body pose image including key nodes of the anatomy and line segments indicating relevance between the key nodes; and
   A2. determining the line segments having relevance to the part of interest in the body pose image.

Alternatively, in step A1 of the long-length imaging method noted above, an identification algorithm of human body pose is employed to locate the key nodes of the anatomy.

Alternatively, in the long-length imaging method noted above, the key nodes include one or more of the following parts: neck, shoulder, wrist, elbow, rib, hip, crotch, knee and ankle.

Alternatively, step A of the long-length imaging method noted above comprises:
   A1'. determining, by using an image segmentation algorithm, a contour of the object in the image presenting the external features of the object to generate a contour image depicting the contour of the object; and
   A2'. determining, in the contour image, a contour portion having relevance to the part of interest according to a proportional relation between every parts of the anatomy of the object in a specific body pose.

Alternatively, in the long-length imaging method noted above, the parts of interest include one of the following parts: spine, leg bone and arm bone.

Alternatively, in the long-length imaging method noted above, the imaging components comprises a X-ray source and a detector.

Alternatively, step B of the long-length imaging method noted above comprises:
   B1. mapping the line segments having relevance to the part of interest in the body pose image to an imageable space of the imaging components;
   B2. determining boundaries of the line segments in the imageable space; and,
   B3. determining the plurality of specified positions of the imaging components based on the boundaries.

Alternatively, in step C of the long-length imaging method noted above, the X-ray images captured at the plurality of specified positions are stitched together with an image stitching algorithm to generate the long-length image in relation to the parts of interest of the anatomy of the object.

In the light of another aspect of the invention, the digital radiography device comprises:
- an imaging unit, comprising a X-ray source and a radiation detector as imaging components;
- a control unit, configured to control an imaging process of the imaging unit based on imaging parameters; and
- an image processing unit configured to:
  - A. determine a part of interest of an anatomy of an object;
  - B. determine, based on the part of interest, the imaging parameters required by the control unit to control the imaging process, the imaging parameters at least including a plurality of specified positions of the imaging components, wherein the plurality of specified positions are configured to make X-ray images captured by the imaging components include the part of interest of the anatomy of the object at the plurality of specified positions; and
  - C. generate a long length image in relation to the part of interest of the anatomy of the object based on the X-ray images captured at the plurality of specified positions.

In the light of another aspect of the invention, image processing system comprises:
- a memory;
- a processor; and,
- a computer program stored in the memory and executable by the processor, wherein the running of the program enables the steps included in the method as delineated above to be implemented.

In the light of another aspect of the invention, the computer-readable memory medium with a computer program stored therein is included, wherein the steps included in the long-length imaging method based on digital radiography as described above are implemented when the computer program is executed by a processor.

In one or more embodiments of this invention, the body pose image suitable to depict the anatomy of the object is employed to determine in the anatomy the boundary of the part of interest within the imageable space and, thus, enable the automatic determination of the plurality of imaging positions, thereby excluding the interference from human factors, simplifying operation steps and eliminating the instability of imaging quality. Moreover, a body pose image is used in the prior art to identify the pose of a human body; however, by diverting it in one or more embodiments of this invention, fast determination of a part of interest in anatomy may be enable. Because of the intuitive form of presentation, this facilitates the operation of users as well. Furthermore, the employment of an identification algorithm of human body pose during generation of a body pose image to identify key nodes may use the algorithm to the maximum advantage in respect of source opening and maturity, which will favor development acceleration and cost reduction.

BRIEF DESCRIPTION ON DRAWINGS

With the following description with figures in every respect, the advantages in above and/or other aspects of this invention will become more explicit and apprehensible more easily. In the figures, the identical or similar units are marked with the same number. The figures comprise:

EMBODIMENTS

This invention will be elaborated more comprehensively in the following parts by reference to the figures depicting schematic embodiments of the invention. However, the invention may be implemented in different forms, and shall not be interpreted as one solely limited to the embodiments presented in the text. The embodiments noted here are intended for a thorough and complete disclosure and, to the end, communicate the protection scope of the invention more comprehensively to persons skilled in the art.

In the Specification, expressions such as "include" and "comprise" are not restricted to indicting that there only exist the units and steps that are described directly and definitely in the Specification and the Claims; instead, the technical solution of this invention does not except the existence of other units and steps that are not directly and definitely described.

Also, expressions like "first" and "second" do not indicate the sequence of units in respect of time, space, size, etc., which, however, are devised purely to differentiate between units.

Figure 1:
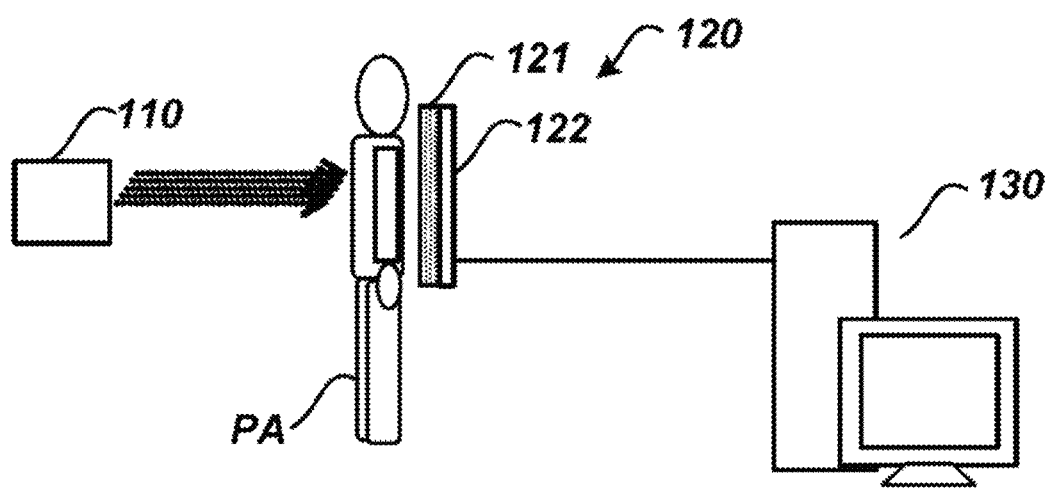
FIG. 1 is a schematic diagram illustrating a digital radiography device of the prior art.
Figure 2:
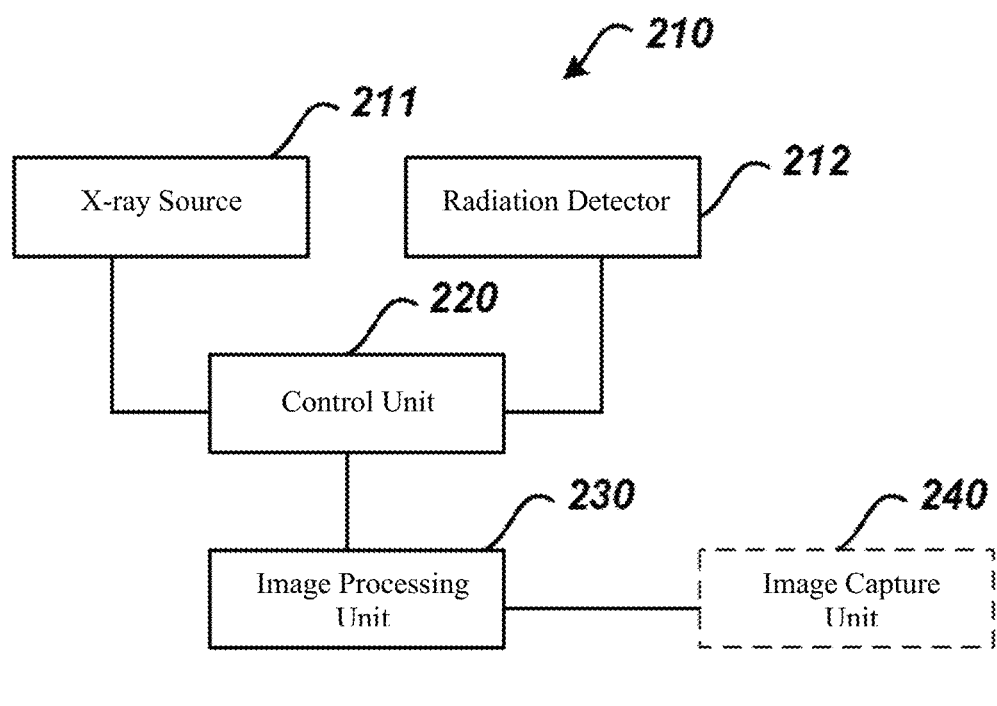
FIG. 2 is a schematic block diagram illustrating the digital radiography device according to an embodiment of this invention.

FIG. 2 is a schematic block diagram illustrating the digital radiography device according to an embodiment of this invention.

A digital radiography device 20, as illustrated by FIG. 2, comprises an imaging unit 210, a control unit 220 and an image processing unit 230. Alternatively, the digital radiography device 20 may further include an image capture device 240 (e.g., camera).

An imaging unit 210 comprises an X-ray source 211 and a radiation detector 212 opposite to the X-ray source 211. In the process of imaging, the radiation generated by the X-ray source 211, after penetrating through a patient or object, beams onto the radiation detector 212. A scintillator screen of the detector converts energy from ionization radiation to light radiation of different frequencies; subsequently, an image sensing array of the detector forms a digital image based on the light radiation. In this embodiment, at least one of the X-ray source 211 and the radiation detector 212 is moveable (e.g., under the control of control unit 220, a motor moves the X-ray source 211 or the radiation detector 212 to an specified position) to image the patient or object.

A control unit 220 is coupled to the imaging unit 210 and configured to control the operation of the imaging unit in an imaging process. For example, the control unit 220 may instruct a motor to move the X-ray source 211 or the radiation detector 212 to an specified position, exert control over the strength and time of exposure and so forth.

In the digital radiography device as illustrated by FIG. 2, an image processing unit 230 is coupled to the radiation detector 212 and configured to process images captured by the radiation detector 212 by diverse means (e.g., configured to stitch together X-ray images captured at a plurality of specified positions by using an image stitching algorithm, adjust the contrast of an image, correct the distorted region of an image and so forth). In this embodiment, the image processing unit 230 is further configured to generate image parameters required in long-length imaging and transmit the generated imaging parameters to the control unit 220. The imaging parameters noted here include but are not limited to, for example, a plurality of specified positions of the X-ray source 211 and/or the radiation detector 211 configured to capture X-ray images, and the overlapping extent of X-ray images captured in adjacent specified positions. The generation mode of the imaging parameters will be delineated in the following parts.

An image capture device 240 (e.g., camera) is coupled to the image processing unit 230 and configured to acquire an image presenting external features of a patient or object. The external features noted here include but are not limited to the external shape of an object, the color, character and texture of the body surface or clothing of an object and so forth.

In this embodiment, the captured image of external features of the patient or object will be used by the image processing unit 230 to generate the imaging parameters. The specific way of such use will be delineated in the following parts. Alternatively, the image capture device 240 may be arranged close to the radiation detector 212 and be made suitable to capture a full-length or half-length image of the patient or object.

Figure 3:
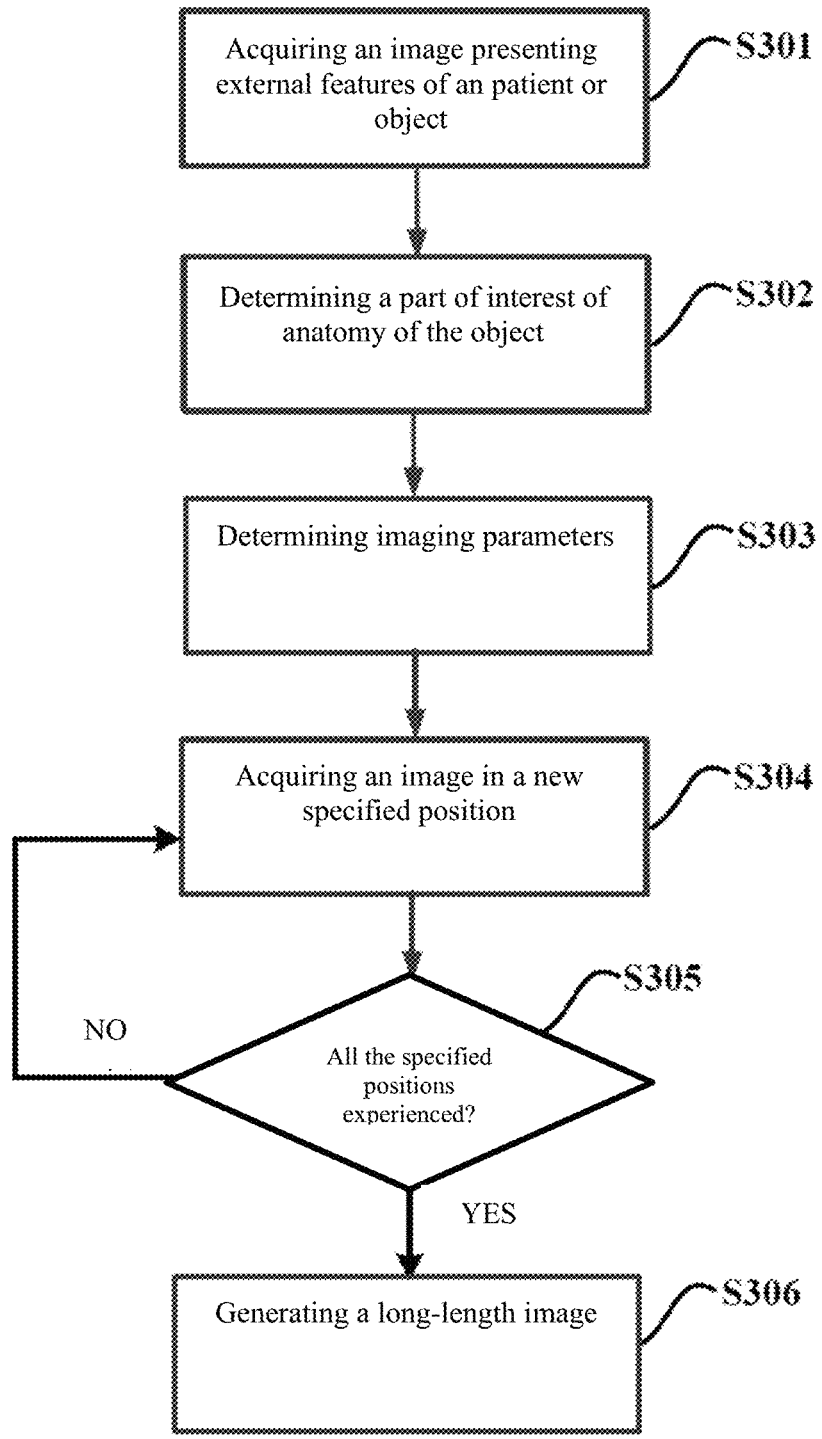
FIG. 3 is a flow chart illustrating the long-length imaging method based on digital radiography according to another embodiment of this invention.

FIG. 3 is a flow chart illustrating the long-length imaging method based on digital radiography according to another embodiment of this invention. As an example, the digital radiography device illustrated in FIG. 2 is used to implement the method of FIG. 3. However, it is necessary to point out that the implementation of the method according to this embodiment is not limited to a digital radiography device with the specific structure shown in FIG. 2.

In step S301 as illustrated in FIG. 3, an image capture device 240 captures an image presenting external features of a patient or object and transmits them to an image processing unit 230. As an example, provided it is required to photograph an X-ray image of the patient's spine, an operator may ask the patient to stand or lie and instruct the image capture device 240 to take an image of the patient's upper-half body (a color image or a black-and-white one).

Subsequently in step S302, the image processing unit 230 determines a part of interest of the anatomy of the object (e.g., spine, leg bone and arm bone). Such a means of determining the part of interest of the anatomy of the object will be delineated below in combination with the embodiment presented in FIG. 4.

In step S303 subsequent to step S302, the image processing unit 230, based on the part of interest determined in step S302, generates imaging parameters required in the implementation of long-length imaging, and transmit them to the control unit 220 so as to use the imaging unit 210 to capture X-ray images at a plurality of specified positions. In this embodiment, the imaging parameters include a plurality of specified positions of imaging components (e.g., an X-ray source 211 and a radiation detector 212). The plurality of specified positions are defined as those where the imaging components are used to capture X-ray images that can include a part of interest of the anatomy of an object. Alternatively, these specified positions may be represented by a time sequence—the order in which the specified positions appear in the time sequence exactly indicates the order in which the X-ray source 211 and the radiation detector 212 appear in such positions. Alternatively, the imaging parameters further include the overlapping extent of the X-ray images captured in adjacent specified positions. Such a means of determining the imaging parameters will be delineated below in combination with the embodiment presented in FIG. 6.

Subsequently in step S304, under the control of control unit 220, the X-ray source 211 and the radiation detector 212 of the imaging unit 210 are positioned in a new specified position in the time sequence so as to capture X-ray images in such a specified position, and the captured X-ray images are transmitted to the image processing unit 230. If this step is executed first time, the new specified position will indicate the initial position of the X-ray source 211 and the radiation detector 212 or the first specified position in the time sequence; if it is not the first time to execute the step, the new specified position will indicate an specified position subsequent immediately to the specified position where the X-ray source 211 and the radiation detector 212 exercise step S304 last time.

Subsequently in step S305, the control unit 220 determines whether all the specified positions in the time sequence have been experienced. If the answer is Yes, the process will go to step S306; otherwise, the process will return to step S304.

In step S306, the image processing unit 230 uses an image stitching algorithm to stitch together the X-ray images captured at the plurality of specified positions so as to generate a long-length image in relation to the part of interest of the anatomy of the object. As an example, provided the radiation detector and the X-ray source move only in one direction, the overlapping extent of the X-ray images captured in the adjacent specified positions may be determined based on the equation below:

$$R_n = X/2 - (H_{n+1} - H_n)/2 \qquad (1)$$

Here, n denotes the sequence number of an specified position, $R_n$ denotes the overlapping extent between an image captured in the $(n+1)^{th}$ imaging position and an image captured in the $n^{th}$ imaging position, X denotes the physical size of a radiation detector in the moving direction, and $H_n$ and $H_{n+1}$ denote the coordinates of the $n^{th}$ imaging position and the $(n+1)^{th}$ imaging position respectively.

Figure 4:
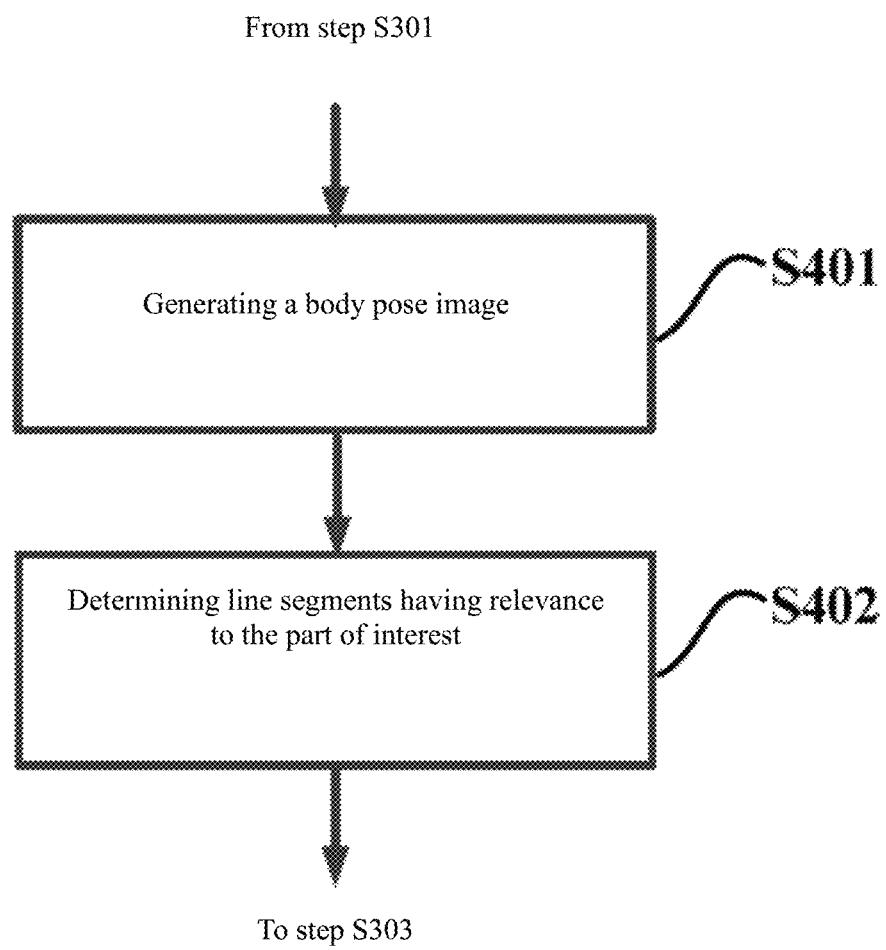
FIG. 4 is a flow chart illustrating the method for determining a part of interest of the anatomy of an object according to another embodiment of this invention.

FIG. 4 is a flow chart illustrating the method for determining a part of interest of the anatomy of an object according to another embodiment of this invention. The method according to FIG. 4 may be applied to step S302 as shown by FIG. 3.

According to step S401 illustrated by FIG. 4, the image processing unit 230 generates a body pose image describing the anatomy of the object by identifying or positioning, in the image presenting the external features of the object, key nodes of the anatomy and by determining the key nodes in pairs having relevance.

The key nodes noted here are ordinarily corresponding to the object's parts with a certain degree of freedom, including but not limited to the parts such as neck, shoulder, wrist, elbow, rib, hip, crotch, knee and ankle.

The relevance noted here may be defined based on the imaging requirement of the anatomy of the object. For example, the digital radiography is often used to image parts, such as the spine, leg bones and arm bones of a patient of object; for this purpose, relevance may be established between the shoulders and the elbows (corresponding to the upper arm bones), between the elbows and the wrists (corresponding to the lower arm bones), between the neck and the crotches (corresponding to the spine), between the crotches and the knees (corresponding to the upper leg bones), between the knees and the ankles (corresponding to the lower leg bones) and so forth. Alternatively, the relevance between the key nodes in pairs may be represented by line segments connecting the key nodes. As the line segments connecting key nodes are used to indicate the relevance, the line segments may represent a specific part of the anatomy (such as upper arm bone, lower arm bone, upper leg bone and spine).

Figure 5A:
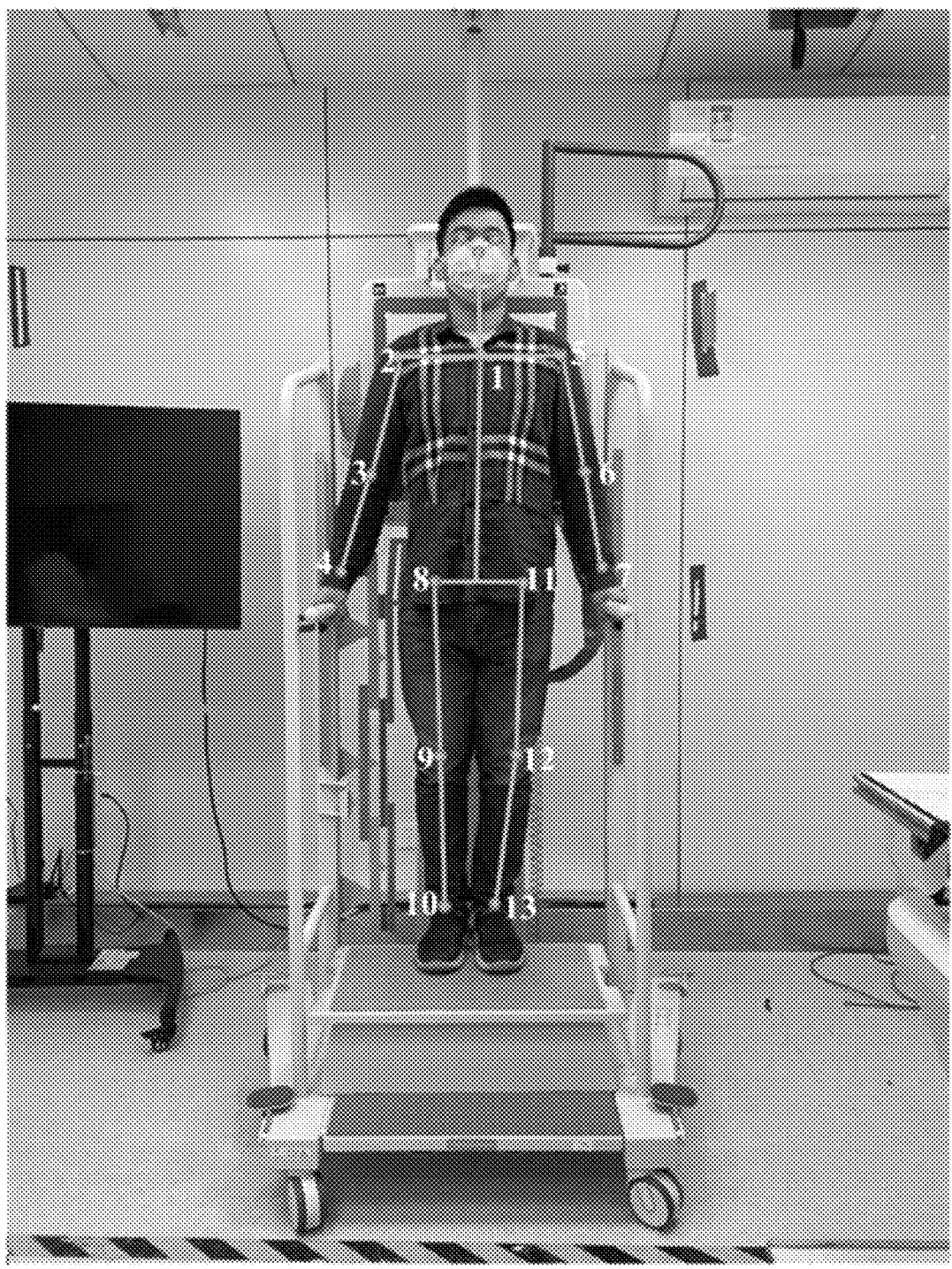
FIG. 5A is a body pose image depicting a front view of the anatomy of an object in the state of standing.
Figure 5B:
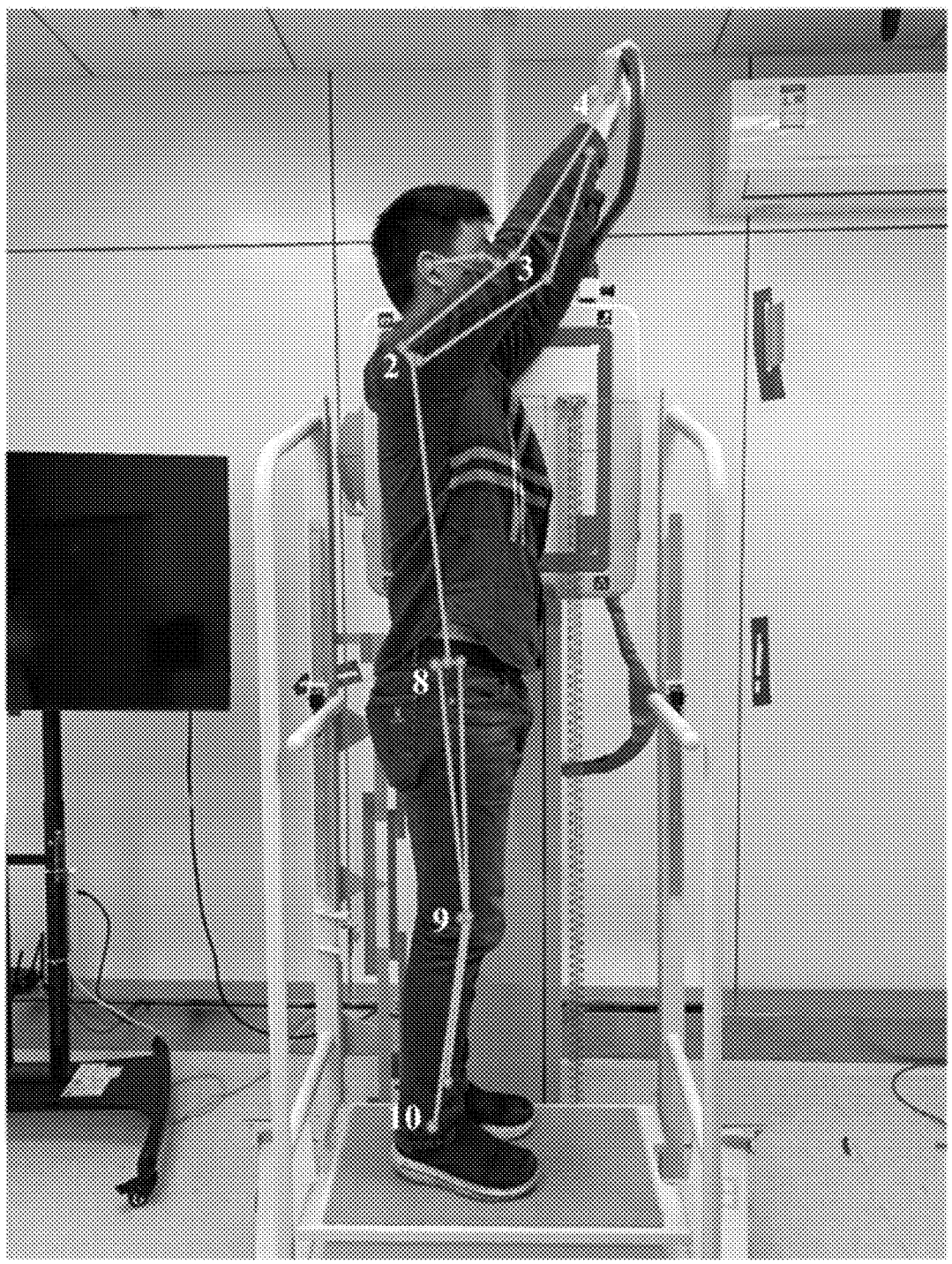
FIG. 5B is a body pose image depicting a side view of the anatomy of an object in the state of standing.

FIG. 5A is a body pose image depicting a front view of the anatomy of an object in the state of standing, and FIG. 5B is a body pose image depicting a side view of the anatomy of an object in the state of standing. As illustrated in FIGS. 5A and 5B, key nodes and line segments therebetween are all drawn on an image presenting the external features of an object; that is, the body pose image presenting the anatomy of the object is drawn by means of overlaying the image presenting the external features of the object.

Referring to FIGS. 5A and 5B, the numbers in the figures are serial numbers denoting the key nodes of the anatomy. For example, "1" denotes neck, "2" and "5" denote shoulders, "3" and "6" denote elbows, "4" and "7" denote wrists, "8" and "11" denote crotches, "9" and "12" denote knees and "10" and "13" denote ankles. In FIG. 5A, when two key nodes are connected by a line segment, relevance will be established between this pair of key nodes; that is, the line segment connecting this pair of key nodes represents a specific part in the anatomy (e.g., the line segment between the key nodes "8" and "9" represents the left upper leg bone or the right upper leg bone).

Identification algorithms of human body, such as Openpose, would usually estimate a human body pose by connecting key points of a human body detected in an image. In step S401, alternatively, the identification algorithm of human body may be employed to generate a body pose image. As shall be noted, although a pose of the object is not necessary for the generation of the imaging parameters in this embodiment, since the human body key points detected by an identification algorithm of human body have a similarity to the key nodes in this embodiment (which is corresponding to parts having a certain degree of freedom on the body of an object), the existing identification features of key points for an identification algorithm of human body may be applied to identification of the key nodes. In terms of the properties of source opening and maturity, the application of identification algorithms of human body to key node identification will favor development acceleration and cost reduction.

Subsequently in step S402, the image processing unit 230 determines the line segments having relevance to the part of interest in a body pose image. As shall be noted, the part of interest here may include not only one specific part of the anatomy (e.g., an upper leg bone, a lower leg bone, an upper arm bone or a lower arm bone), but also a plurality of specific parts of the anatomy (e.g., a complete leg bone or a complete arm bone). That is, the line segment having relevance to the part of interest may be one or a plurality of line segments in a body pose image.

Figure 6:
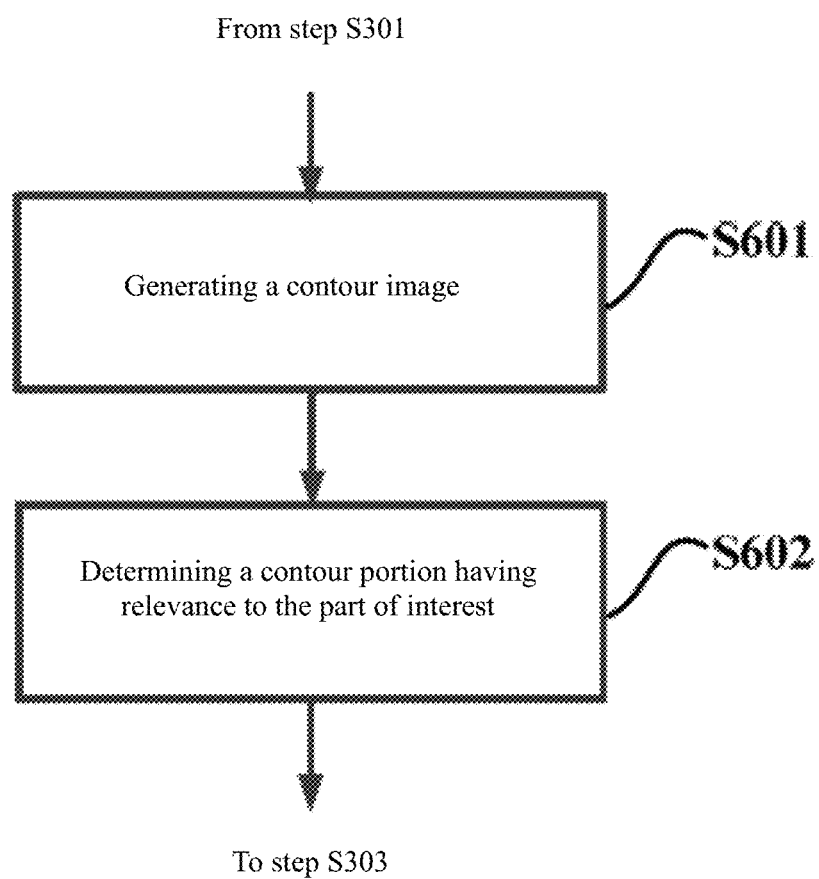
FIG. 6 is a flow chart illustrating the method for determining a part of interest of the anatomy of an object according to another embodiment of this invention.

FIG. 6 is a flow chart illustrating the method for determining a part of interest of the anatomy of an object according to another embodiment of this invention. The method illustrated by FIG. 6 may be applied to step S302 shown in FIG. 3.

Figure 7:
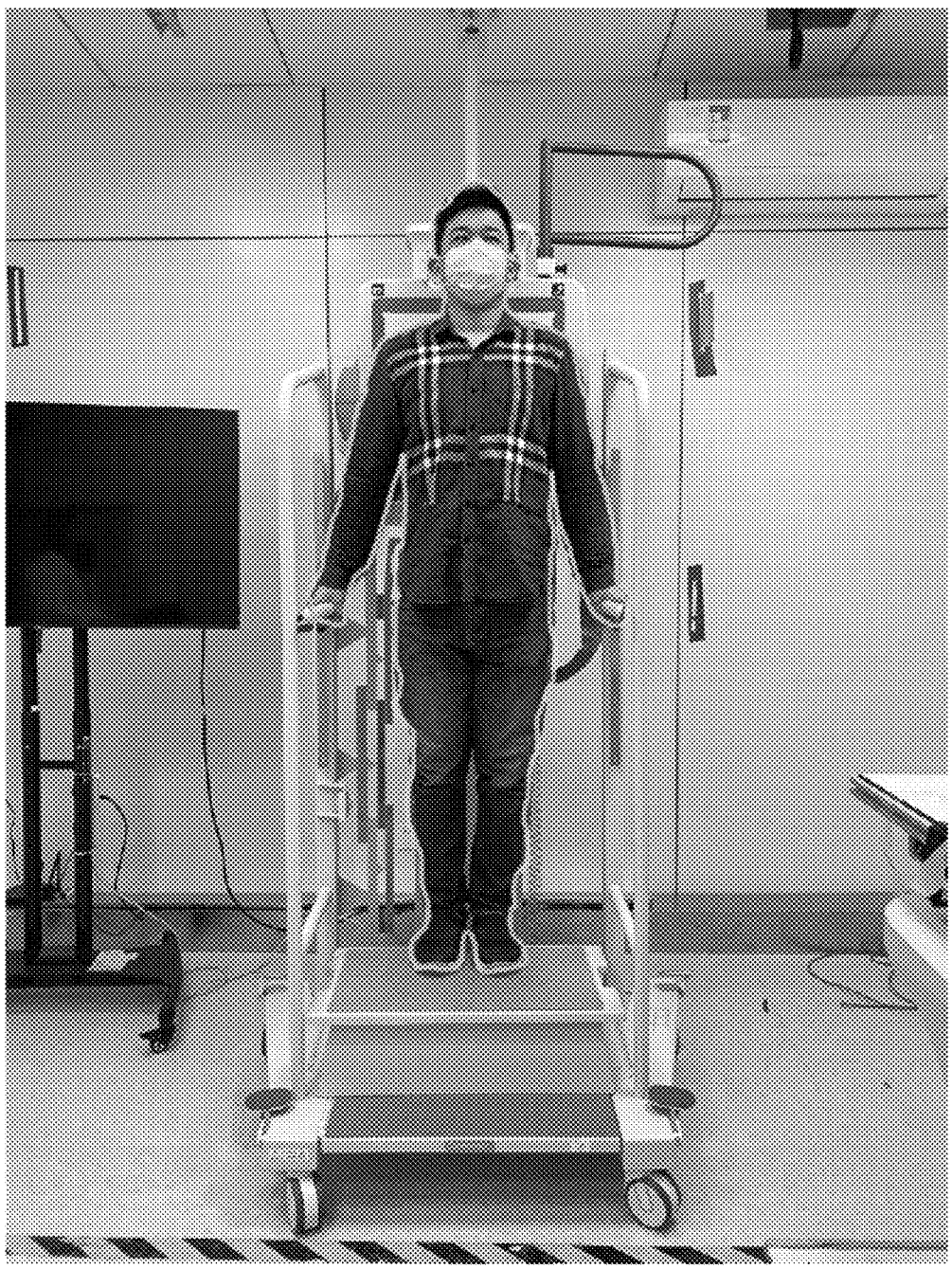
FIG. 7 shows an example embodying the use of an image segmentation algorithm to determine a contour of an object in an image presenting external features of the object.

In step S601 as illustrated by FIG. 6, the image processing unit 230 uses an image segmentation algorithm to determine an contour of the object in the image presenting external features of the object so as to generate a contour image describing the object's contour. The example cited here in relation to the image segmentation algorithm includes but is not limited to segmentation algorithms based on threshold values, segmentation algorithms based on areas, segmentation algorithms based on edges and so forth. FIG. 7 gives an example about determining a contour of an object in an image presenting external features of the object with an image segmentation algorithm.

Subsequently in step S602, the image processing unit 230 determines a contour portion having relevance to the part of interest according to a proportional relation between every parts of the anatomy of the object in a specific body pose. As an example, the proportional relation between every parts of the anatomy may be determined based on the statistic derived from a large quantity of samples. Moreover, though the proportional relation between every parts of the anatomy might vary due to a change in the body pose, only a small number of types of poses would normally be used during digital photography and, therefore, the requirements of application would be met by storing the proportional relations corresponding to these poses in advance and invoking them when they are needed for use.

The relevance noted here is also defined based on the imaging requirement of the anatomy of the object. For example, as digital radiography is used to image the parts such as the spine, the leg bone and the arm bone of the patient or object, the contour portions determined are respectively the contours of parts such as the trunk, the upper leg and the arm.

Figure 8:
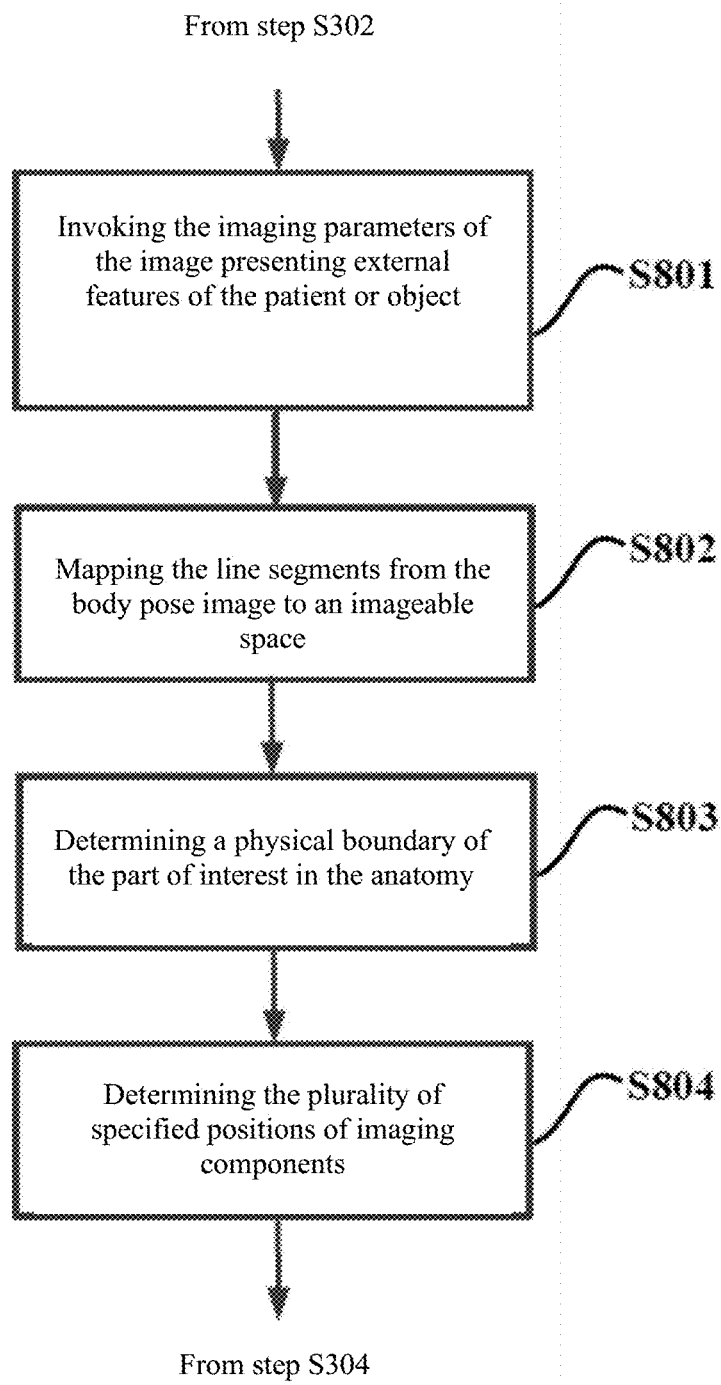
FIG. 8 is a flow chart illustrating the method for determining imaging parameters according to another embodiment of this invention.

FIG. 8 is a flow chart illustrating the method for determining imaging parameters according to another embodiment of this invention. The method illustrated by FIG. 8 may be applied to step S303 shown in FIG. 3.

Once the imaging parameters of the external features of the patient or object (e.g., focus) are determined, the line segments indicating the parts of interest of the anatomy may be mapped from the body pose image into a real physical space (e.g., an imageable space of the imaging components), or contour portions indicating the parts of interest of the anatomy may be mapped from the contour image into a real physical space (e.g., an imageable space of the imaging components). The imageable space noted here refers to such a space, in which, by moving the imaging components to every accessible position, the patient or object may be imaged by the imaging components (e.g., the X-ray source and the radiation detector), and out of which the patient or object may not be imaged by the imaging components (e.g., the X-ray source and the radiation detector).

In another aspect, the line segment indicates the extension range or boundary of the part of interest of the anatomy in the body pose image. Since the extension range has a unique corresponding extension range or boundary in the real physical space, the coordinates of the part of interest of the anatomy in the imageable space may be obtained by mapping the body pose image to the imageable space (i.e., conversion of the coordinates), whereby corresponding imaging parameters are determined.

In terms of the contour portion of the part of interest of the anatomy, its boundary in the contour image also has a unique corresponding extension range or boundary in the real physical space; thus, the coordinates of the part of interest of the anatomy in the imageable space may be obtained by mapping the contour image to the imageable space (i.e., conversion of the coordinates), whereby corresponding imaging parameters are determined.

In step S801 as illustrated by FIG. 8, the image processing unit 230 invokes the imaging parameters of the image presenting the external features of the patient or object.

Subsequently into step S802, the image processing unit 230, based on the invoked imaging parameters, maps the line segments having relevance to the part of interest in the body pose image, or the contour portion corresponding to the part of interest in the contour image, to the imageable space of the imaging components. For example, the coordinates of every point of the line segments bearing the relevance in the body pose image, and the coordinates of every points of the contour bearing the relevance in the contour image, will be converted into corresponding coordinates in the imageable space.

Subsequently into step S803, the image processing unit 230, based on the coordinates of the line segments bearing the relevance in the imageable space, determines a physical boundary of the part of interest in the anatomy (e.g., in a two-dimensional rectangular coordinate system parallel to a imaging plane, the physical boundary may be represented by the maximum and minimum values of a part of interest on the X and Y axes).

Upon step S803, the method process illustrated in FIG. 8 goes to step S804. In the step, the image processing unit 230, based on the boundary determined by step S803, determines the plurality of specified positions of the imaging parameters or imaging components. As an example, the total times of imaging or exposure may be determined first; next, the position of the radiation detector and the X-ray source are determined every time imaging is excised (e.g., the stop position of at center of the radiation detector and the X-ray source). In the example, provided the radiation detector and the X-ray source move along the X axis, the total times of imaging or exposure may be determined according to the equation below.

$$N = \text{int}\left(\frac{L-P}{L_d - P} + 1\right) \quad (2)$$

Here, N is the total times of imaging or exposure; int, as an operational character, denotes the acquisition of integer part; L denotes the length of a part of interest; $L_d$ indicates the effective exposure length of the radiation detector every time exposure is exercised; and, P refers to the minimum exposure overlapping necessary for image stitching.

Correspondingly, the position of the radiation detector and the X-ray source every time imaging is excised may be determined according to the equation below.

$$H_N = \begin{cases} H_{ini} + \frac{L_d}{2} + n \times (L_d - P) \text{ if } n = 1, 2 \ldots \ldots N-1 \\ H_{N-1} + (L - (N-2)) \times L_d + (N-3) \times P)/2 \text{ if } n = N \end{cases} \quad (3)$$

Here, $H_n$ denotes the position where the radiation detector and the X-ray source are at the $n^{th}$ time of imaging or exposure; and $H_{ini}$ denotes the limit position of the radiation detector and the X-ray source on the X axis (the minimum allowed value of the X axis).

Figure 9:
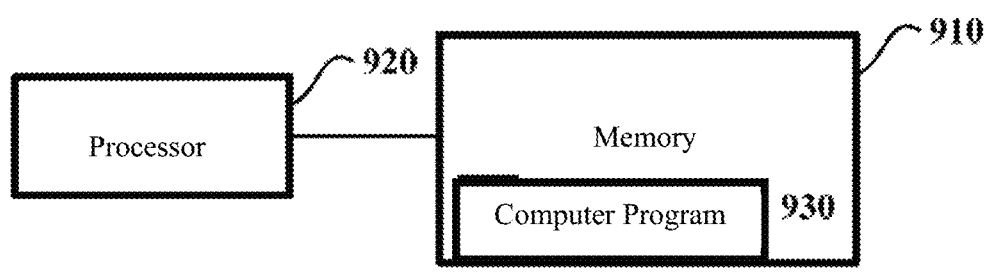
FIG. 9 is a schematic block diagram illustrating the image processing system according to another embodiment of this invention.

FIG. 9 is a schematic block diagram illustrating the image processing system according to another embodiment of this invention. The image processing unit shown in FIG. 2 may be enabled by the image processing system of the embodiment.

An image processing system 90, as illustrated by FIG. 9, includes a memory 910 (non-volatile memory such as flash memory, ROM, hard disk driver, magnetic disk, compact disk), a processor 920 and a computer program 930 stored in the memory 910 and executable in the processor 920.

In the image processing system illustrated in FIG. 9, the computer program 930 is executed to implement the steps included in the long-length imaging method based on digital radiography as described by FIGS. 3-8.

According to another aspect of the invention, a computer-readable memory medium with a computer program stored therein is provided. And, the steps included in the long-length imaging method based on digital radiography as described by FIGS. 3-8 may be implemented when the computer program is executed.

The embodiments and examples are offered in the text to elaborate the implementation mode according to the technology and its specific applications in the best way such that one skilled in the art could implement and use the present invention. However, as known to all those skilled in the art, the above description and examples are offered solely for explanation and example citation, and the given description is not intended to cover all the respects of this invention or limit it to the forms exactly disclosed.

The invention claimed is:

1. A long-length imaging method based on digital radiography, the method comprising the steps of:
   determining a part of interest of an anatomy of an object;
   generating, from an image of the object captured by a camera, a body pose image suitable to depict the anatomy of the object, the body pose image highlighting key nodes of the anatomy and highlighting line segments between the key nodes of the anatomy, the key nodes of the anatomy indicating bone joints of the anatomy;
   determining which of the line segments in the body pose image have relevance to the part of interest of the anatomy of the object;
   determining imaging parameters of digital radiography based on the part of interest and the relevant line segments, the imaging parameters including a plurality of specified positions of an X-ray source and a digital X-ray detector, wherein the plurality of specified positions are configured to capture X-ray images including the part of interest of the anatomy of the object; and
   generating a long-length image of the part of interest of the anatomy of the object including stitching together the captured X-ray images.

2. The long-length imaging method according to claim 1, further comprising employing an identification algorithm of a human body pose to locate the key nodes of the anatomy.

3. The long-length imaging method according to claim 1, further comprising including one or more of a neck, shoulder, wrist, elbow, rib, hip, crotch, knee and ankle as a key node.

4. The long-length imaging method according to claim 1, further comprising:
   determining, by using an image segmentation algorithm, a contour of the object in the image presenting the external features of the object to generate a contour image depicting the contour of the object; and determining, in the contour image, a contour portion having relevance to the part of interest according to a proportional relation between every parts of the anatomy of the object in a specific body pose.

5. The long-length imaging method according to claim 1, wherein the part of interest includes one of the following parts: spine, leg bone and arm bone.

6. The long-length imaging method according to claim 1, further comprising:

mapping the line segments having relevance to the part of interest in the body pose image to an imageable space of the imaging components;

determining boundaries of the line segments in the imageable space; and determining the plurality of specified positions of the imaging components based on the boundaries.

7. An image processing system, comprising:
a memory;
a processor; and,
a computer program stored in the memory and executable by the processor, wherein execution of the computer program causes the steps of claim 1 to be executed.

8. A digital radiography device, comprising:
an imaging unit, comprising an X-ray source, a camera, and a radiation detector as imaging components;
a control unit, configured to control an imaging process of the imaging unit based on imaging parameters; and
an image processing unit configured to:
determine a part of interest of an anatomy of an object;
generate, from an image of the object captured by the camera, a body pose image suitable to depict the anatomy of the object, the body pose image highlighting key nodes of the anatomy and highlighting line segments between the key nodes of the anatomy, the key nodes of the anatomy indicating bone joints of the anatomy;
determine which of the line segments in the body pose image have relevance to the part of interest of the anatomy of the object;
determine, based on the part of interest and the relevant line segments, the imaging parameters required by the control unit to control the imaging process, the imaging parameters including a plurality of specified positions of the imaging components, wherein the plurality of specified positions are configured to capture X-ray images of the part of interest of the anatomy of the object at the plurality of specified positions; and generate a long length image of the part of interest of the anatomy of the object including stitching together the X-ray images captured at the plurality of specified positions.

9. The digital radiography device according to claim 8, wherein an identification algorithm of a human body pose is employed to locate the key nodes of the anatomy.

10. The digital radiography device according to claim 8, wherein the image processing unit is further configured to execute the following steps:

determining, by an image segmentation algorithm, a contour of the object in the image presenting the external features of the object to generate a contour image depicting the contour of the object; and determining, in the contour image, a contour portion having relevance to the part of interest according to a proportional relation between every parts of the anatomy of the object in a specific body pose.

11. The digital radiography device according to claim 8, wherein the key nodes include one or more of the following parts: neck, shoulder, wrist, elbow, rib, hip, crotch, knee and ankle.

12. The digital radiography device according to claim 8, wherein the part of interest includes one of the following parts: spine, leg bone and arm bone.

13. The digital radiography device according to claim 8, wherein the image processing unit is further configured to execute the following steps:

mapping the line segments having relevance to the part of interest in the body pose image to an imageable space of the imaging components;

determining boundaries of the line segments in the imageable space; and determining the plurality of specified positions of the imaging components based on the boundaries.

\* \* \* \* \*